United States Patent [19]
Fujita et al.

[11] Patent Number: 5,474,076
[45] Date of Patent: Dec. 12, 1995

[54] BLOOD PRESSURE MEASURING APPARATUS

[75] Inventors: Hisahiro Fujita, Yamatokoriyama; Yoichi Kato; Toshio Furukawa, both of Nara, all of Japan

[73] Assignee: Sharp Kabushiki Kaisha, Osaka, Japan

[21] Appl. No.: 276,182

[22] Filed: Nov. 25, 1988

[30] Foreign Application Priority Data

Nov. 25, 1987 [JP] Japan ................................. 62-297238

[51] Int. Cl.$^6$ ........................................................ A61B 5/02
[52] U.S. Cl. ............................................................ 128/683
[58] Field of Search ............................. 128/672, 677–686

[56] References Cited

U.S. PATENT DOCUMENTS

| | | | |
|---|---|---|---|
| 3,508,537 | 4/1970 | Kahn et al. | 128/683 |
| 3,552,383 | 1/1971 | Krueger et al. | 128/682 |
| 4,326,536 | 4/1982 | Kitagawa et al. | 128/682 |
| 4,660,567 | 4/1987 | Kaneko et al. | 128/682 |
| 4,671,290 | 6/1987 | Miller et al. | 128/681 |
| 4,712,564 | 12/1987 | Yamaguchi | 128/682 |

FOREIGN PATENT DOCUMENTS

| | | |
|---|---|---|
| 55-151942 | 4/1979 | Japan . |
| 55-138440 | 5/1979 | Japan . |
| 57-145640 | 2/1981 | Japan . |

*Primary Examiner*—Lee S. Cohen
*Assistant Examiner*—John P. Lacyk
*Attorney, Agent, or Firm*—Morrison & Foerster

[57] ABSTRACT

A blood pressure measuring apparatus which comprises: a memory which stores the pressure value of a cuff when the cuff is to be pressurized again after the cuff has been pressurized; a comparator which, after the cuff is pressurized again, compares the pressure value of the cuff with the stored pressure value; a controller which produces an additional driving signal when the former in not greater than the latter; and a pump which pressurizes again the cuff in response to the additional driving signal.

3 Claims, 4 Drawing Sheets

5,474,076

BLOOD PRESSURE MEASURING APPARATUS

BACKGROUND OF THE INVENTION

1. Field of the Invention

This invention relates to a blood pressure measuring apparatus such as a so-called hematomanometer, tonometer or the like. More particularly, it relates to a blood pressure measuring apparatus having a pressurizing means which is operated by a driving means such as an electric motor.

2. Description of the Prior Art

A blood pressure measuring apparatus which is electronically controlled has a pump for supplying pressurized air to a pressure applying means such as a so-called cuff. The pump is driven by a small electric motor. The motor is controlled by a suitable electronic control means having a CPU. When the pressure of the cuff is insufficient, the pump is operated to restart the pressurization. Hereinafter, such a operation is referred as "repressurization". A conventional blood pressure measuring apparatus often fails to start the repressurization because of the stiffness of the pump.

A blood pressure measuring apparatus of the prior art will be described with reference to FIGS. 2A to 2C. The apparatus shown in FIG. 2A comprises a DC motor 1, a CPU 2, a transistor 3, a pump 4, and resistors R1 and R2. The motor 1 is mechanically connected to the pump 4 via an accentric shaft 5 and an operating rod 6 connected to a diaphragm 4a (FIGS. 2B and 2C). The pump 4 has a check valve (not shown in FIGS. 2A to 2C). When the output signal of the CPU 2 is low and the transistor 3 is off, a voltage $V_p$ is not applied to the motor 1 so that the pump 4 is not operated. When a cuff (not shown here) is to be pressurized, the output signal of the CPU 2 becomes high to turn the transistor 3 on. Then, the pump 4 is driven by the motor 1 to supply compressed air to the cuff. When the pressure of the cuff is increased, the output signal of the CPU 2 becomes low so that the motor 1 stops, resulting in that the diaphragm 4a and the rod 6 are positioned at their highest position, owing to the pressure of the cuff.

If the pressure of the cuff is insufficient, the output signal of the CPU 2 becomes high again so as to start the repressurization. In this case, the motor 1 must rotate the shaft 5 against the pressure in the pump 4. Namely, the shaft 5 must be driven by a force which is greater than the pressure in the pump 4. In order to facilitate the repressurization, the CPU 2 of the improved apparatus outputs a driving signal for repressurization (hereinafter, referred as "repressurization signal") which consists of one short pulse P1 between times t1 and t2 and a long pulse P2 between times t3 and t4, as shown in FIG. 3. Alternatively, the repressurization signal of the CPU 2 may consist of two or more short pulses P1 and a long pulse P2, as shown in FIG. 5.

At the time t1 the CPU 2 outputs the repressurization signal of FIG. 3, and the motor 1 begins to rotate in the forward direction indicated in FIG. 4A, so that the operating rod 6 moves downward. When the force of the motor 1 is inadequate, it fails to make a turn as large as 180 deg., and the repressurization signal falls in this state (time t2), resulting in that the operating rod 6 ceases the downward movement and begins to be forced back by the pressure of the pump 4 (FIG. 4B).

The operating rod 6 thus forced back causes the shaft 5 to rotate in the reverse direction. When the shaft 5 has passed the upper dead point, the repulsive force of the pressure medium (air) of the pump 4 begins to cause the shaft 5 and motor 1 to rotate in the forward direction. Under this state, the repressurization signal becomes high again (time t3). The turning force owing to the pressure medium of the pump 4 cooperates with the turning force of the motor 1 in applying a greater force to the shaft 5 in the forward direction. In other words, the repulsive force of the pump 4 gives an impetus to the shaft 5. Hence, the turning force applied to the shaft 5 surpasses the counter force produced by the pump 4, so that the motor 1 can continue to rotate in the forward direction (FIG. 4C).

If it is not sufficient in producing an ample amount of the impetus force by one pulse P1, the repressurization signal may have two or more short pulses which are produced in series, as shown in FIG. 5.

In the above-described apparatus, the starting properties of the motor under the condition that the cuff has been already pressurized is improved. Even when a small electric motor is used as the motor 1, consequently, it can drive the pump 4 to conduct the repressurization.

The width, duration and number of the short pulse(s) P1 and also the timing of the application of the pulse are suitably set in accordance with many factors such as the size and material of the diaphragm 4a and the degree of eccentricity of the shaft 5, so that the pulse(s) P1 is applied adequately.

However, these factors vary depending upon the size or type of the apparatus, or, in some cases, upon each individual apparatus even when the size or type is same, resulting in that such an apparatus sometimes fails to conduct the repressurization and that the pressure of the cuff cannot be raised to a level for an adequate pressure measurement. In a conventional apparatus, therefore, the timing must be precisely adjusted, which complicates the manufacturing process. The above-described apparatus still remains to be further improved.

SUMMARY OF THE INVENTION

The blood pressure measuring apparatus of this invention, which overcomes the above-discussed and numerous other disadvantages and deficiencies of the prior art, comprises a pressure applying means, a measuring means which measures the pressure of said pressure applying means, a control means which produces a driving signal, and a pressure means which pressurizes said pressure applying means in response to said driving signal, said apparatus further comprises: a memory means which stores the pressure value of said pressure applying means when said pressure applying means is to be pressurized again after said pressure applying means has been pressurized; and a comparing means which, after said pressure applying means is pressurized again, compares the pressure value of said pressure applying means with said stored pressure value, said control means produces an additional driving signal when the former is not greater than the latter, and said pressure means pressurizes again said pressure applying means in response to said additional driving signal.

In a preferred embodiment, the additional driving signal comprises one short pulse at its top.

In a preferred embodiment, the additional driving signal comprises two or more short pulses at its top.

In a preferred embodiment, the control means produces repeatedly said additional driving signal until the pressure of said pressure applying means reaches a predetermined value.

Thus, the invention described herein makes possible the objectives of (1) providing a blood pressure measuring apparatus which can conduct the repressurization reliably; and (2) providing a blood pressure measuring apparatus which can obviate the necessity of a precise adjustment of the driving signal.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Example

Figure 1:
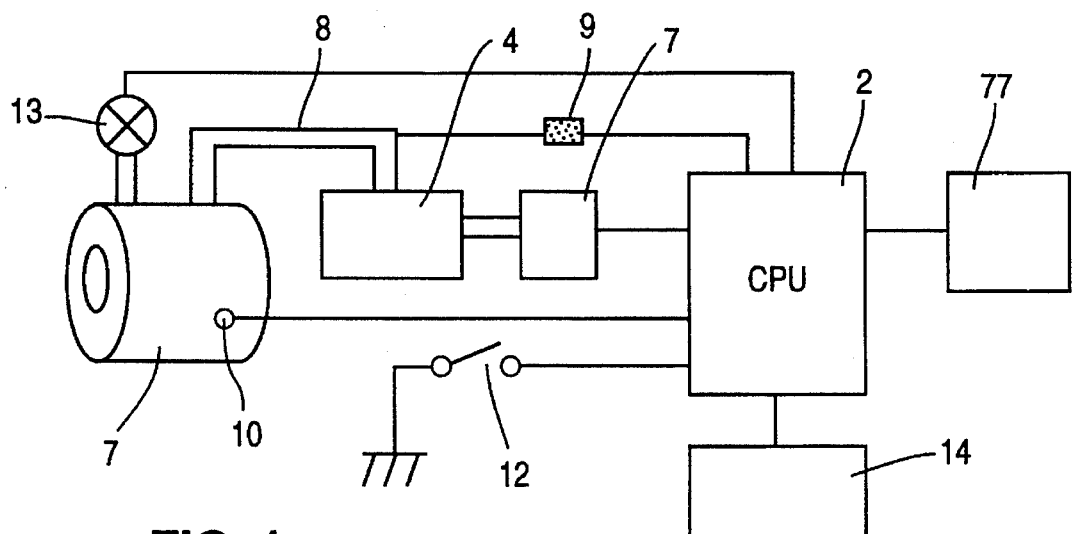
FIG. 1 is a block diagram illustrating a blood pressure measuring apparatus according to the invention.
Figure 2A:
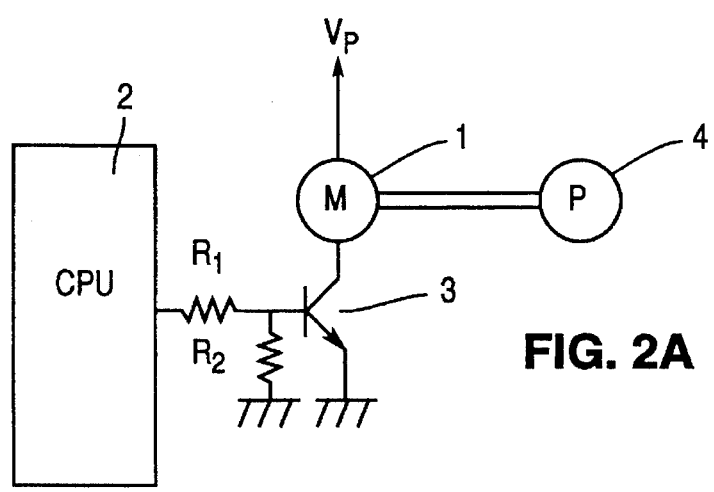
FIG. 2A is a diagram illustrating an improved blood pressure measuring apparatus.
Figure 2B:
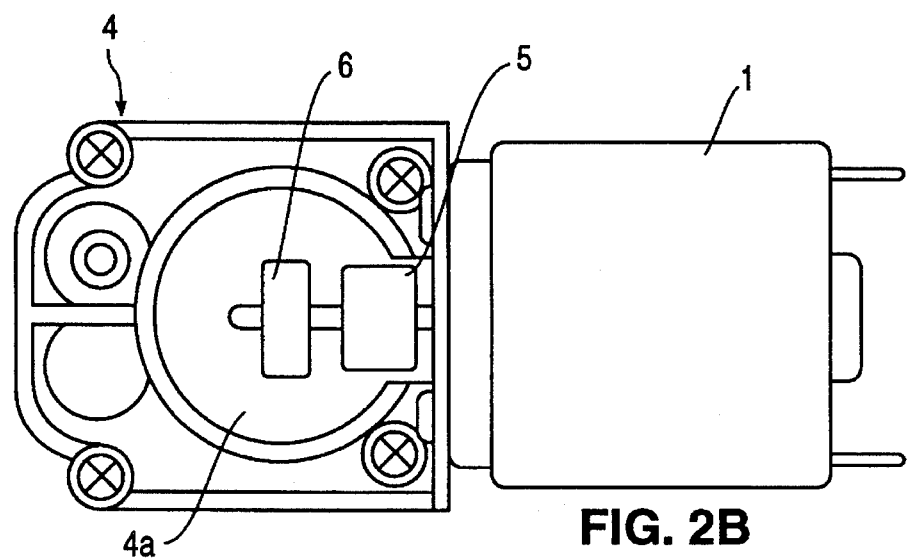
FIGS. 2B and 2C are a plan view and side view showing the combination of a motor and a pump in the apparatus of FIG. 2A, respectively.
Figure 2C:
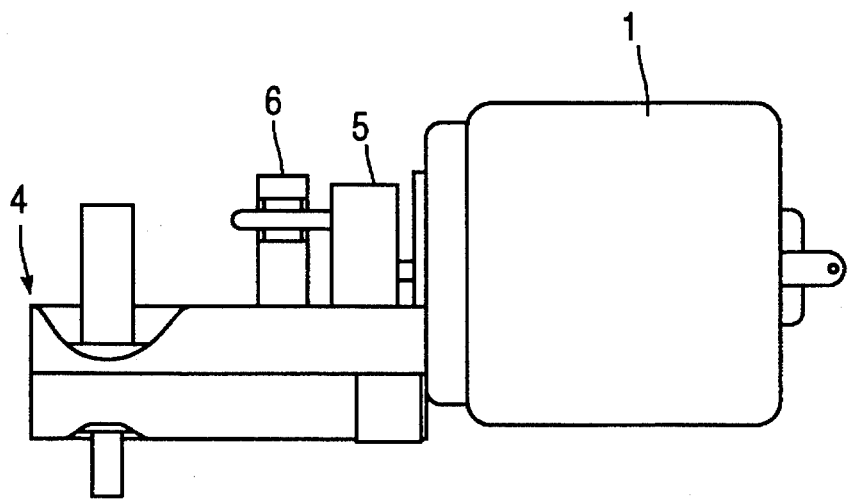

FIG. 1 illustrates diagrammatically one embodiment of the blood pressure measuring apparatus of this invention. The apparatus of FIG. 1 comprises a DC motor 1, a CPU 2, a pressurizing pump 4, a cuff 7, a memory 11, a display device 14 such as an LCD, and a switch 12. The memory 11 stores the program executed by the CPU 2. The pump 4 and the cuff 7 are connected to each other through a pipe 8. The pressure in the pipe 8 (i.e., the pressure of the cuff 7) is detected by a pressure sensor 9 attached to the pipe 8, and the detected pressure value is input to the CPU 2. A Korotkoff sound sensor 10 is disposed on the cuff 7. The CPU 2 detects the appearance and disappearance of the Korotkoff sound on the basis of the output of the sensor 10. The cuff 7 is wound around a portion of the body of a subject so as to press blood vessels therein.

Figure 3:
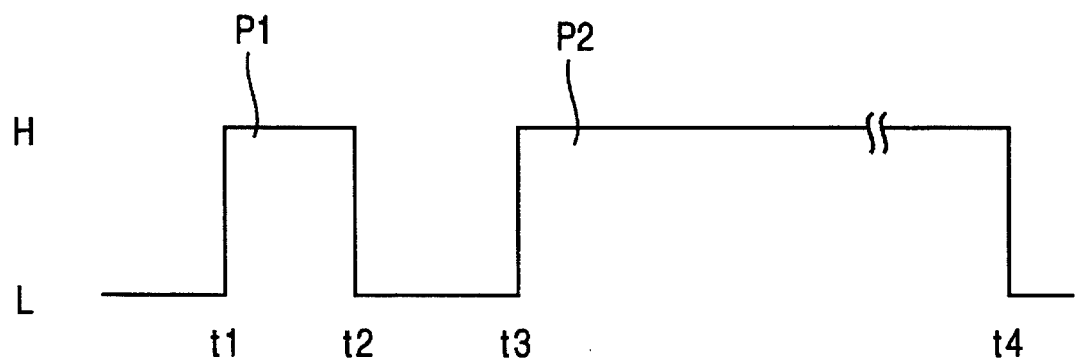
FIG. 3 shows a wave form of a driving signal.
Figure 4A:
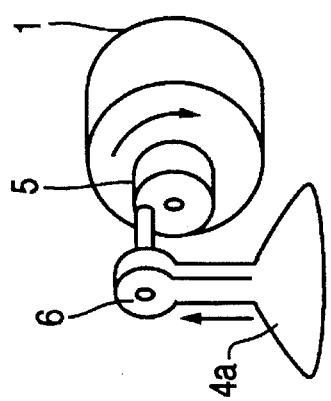
FIGS. 4A to 4C illustrate the relation between the eccentric shaft and the diaphragm of the pump.
Figure 4B:
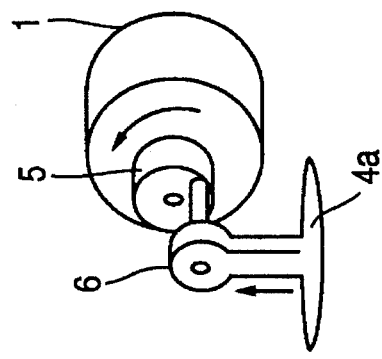
Figure 4C:
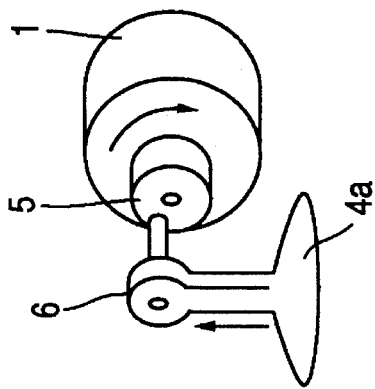
Figure 5:
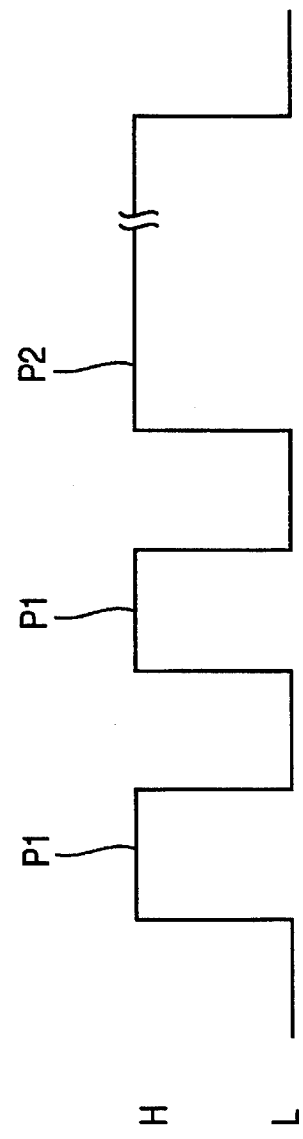
FIG. 5 shows another wave form of a driving signal.

When the switch 12 is closed, the CPU 2 supplies a driving signal to the motor 1. The pump 4 is driven by the motor 1 to start the pressurization of the cuff 7. The cuff 7 is required to be pressurized up to a pressure which is slightly higher than the maximal blood pressure of a subject. When the CPU 2 judges that the pressure of the cuff 7 is insufficient, the pressure value at this time is stored in the memory 11, and the CPU 2 produces a repressurization signal and supplies it to the motor 1. The repressurization signal may have one short pulse P1 and a long pulse P2 as the driving signal shown in FIG. 3, or have two or more short pulses P1 and a long pulse P2 as the driving signal shown in FIG. 5. The motor 1 drives the pump 4 to conduct the repressurization in the same manner as described above.

After conducting the repressurization, the CPU 2 compares the pressure value detected by the pressure sensor 9 with the pressure value stored in the memory 11. If the pressure value after the repressurization is not greater than the stored pressure value (namely, the repressurization has not been conducted, or the motor 1 has failed to rotate), the CPU 2 produces repeatedly an additional repressurization signal until the pressure of the cuff 7 reaches the required value. After the pressure of the cuff 7 has reached the required value, an exhaust valve 13 attached to the cuff 7 is opened partly so that the pressure of the cuff 7 is gradually decreased.

During this pressure reduction process, the maximal and minimal blood pressures are measured. Namely, the blood pressure at the time when the Korotkoff sound appears is measured as the maximal blood pressure, and that at the time when the Korotkoff sound disappears is measured as the minimal blood pressure. The measured values of the maximal and minimal blood pressures are stored in the memory 11, and displayed by the display device 14. Thereafter, the valve 13 is fully opened to discharge rapidly the air in the cuff 7.

Figure 6:
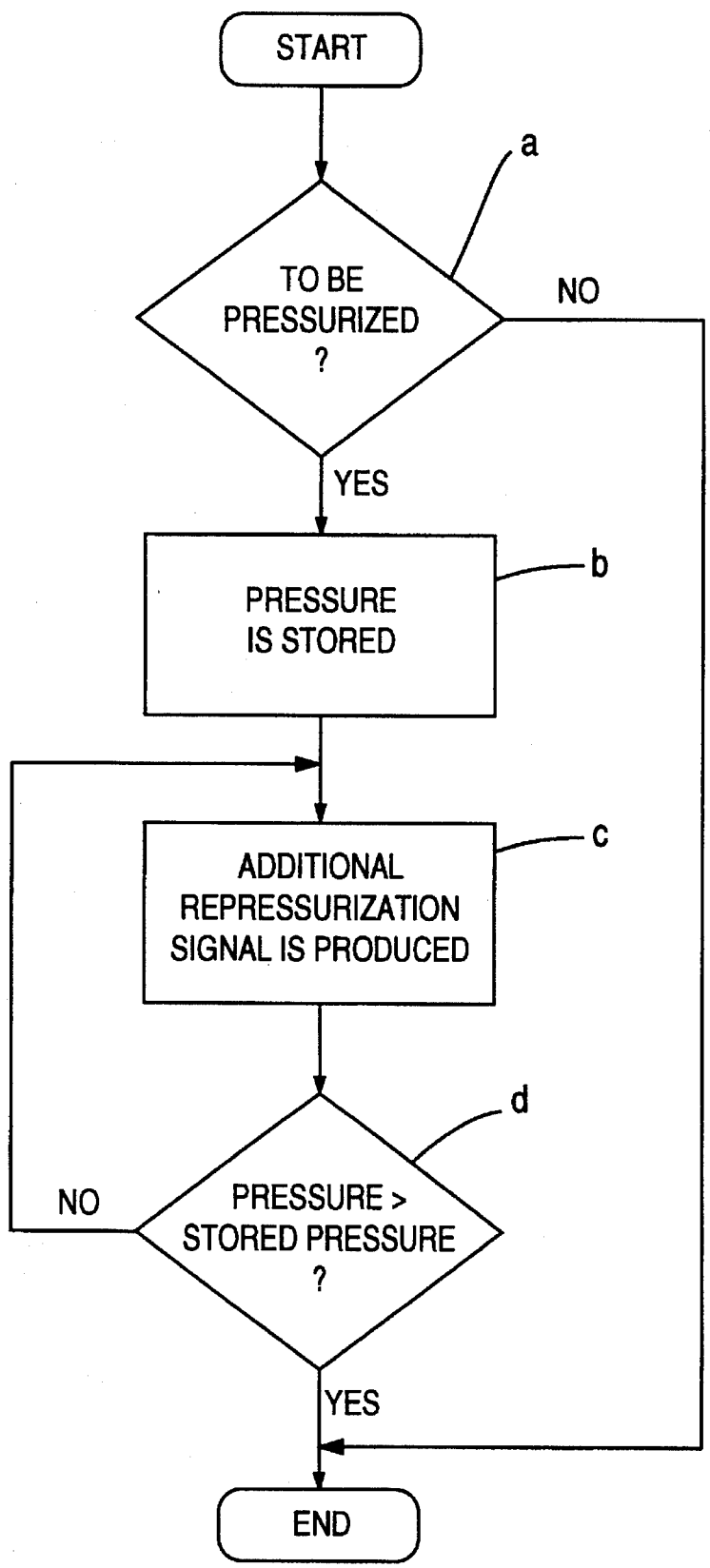
FIG. 6 is a flow chart of a control process according to the invention.

The control process will be summarized with reference to the flow chart which is shown in FIG. 6. In step a, the CPU 2 judges whether the repressurization is necessary or not. If not, the repressurization is not conducted. When the repressurization is to be conducted, the pressure value of the cuff 7 is stored in the memory 11 (step b), and the CPU 2 produces the additional repressurization signal to drive the pump 4 (step c). After transmitting the additional repressurization signal, the CPU 2 compares the pressure value of the cuff 7 with the pressure value stored in the memory 11 (step d). If the pressure value of the cuff 7 is not greater than the stored value (i.e., the repressurization has not been conducted sufficiently), the process returns to step c, and the additional repressurization signal is repeatedly produced until the pressure value of the cuff 7 becomes greater than the stored pressure value (or than the sum of the stored pressure value and a predetermined value).

When the present invention is applied to a blood pressure measuring apparatus of the oscillometric type, the apparatus is provided with various sensors for detecting a pulse wave signal.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. In a blood pressure measuring apparatus, comprising a pressure applying means, a measuring means which measures the pressure of said pressure applying means, a control means which produces a driving signal, and a pressure means which pressurizes said pressure applying means in response to said driving signal, said apparatus further comprises:

a memory means which stores the pressure value of said pressure applying means when said pressure applying means is to be pressurized again after said pressure applying means has been pressurized; and a comparing means which, after said pressure applying means is pressurized again, compares the pressure value of said pressure applying means with said stored pressure value, said control means produces an additional driving signal when the former is not greater than the latter, and said pressure means pressurizes again said pressure applying means in response to said additional driving signal, wherein said additional driving signal comprises one short pulse at its beginning.

2. A blood pressure meeting apparatus according to claim 1, wherein said additional driving signal comprises two or more short pulses at its beginning.

3. In a blood pressure measuring apparatus, comprising a pressure applying means, a measuring means which measures the pressure of said pressure applying means, a control means which produces a driving signal, and a pressure means which pressurizes said pressure applying means in response to said driving signal, said apparatus further comprises:

a memory means which stores the pressure value of said pressure applying means when said pressure applying means is to be pressurized again after said pressure applying means has been pressurized; and a comparing means which, after said pressure applying means is pressurized again, compares the pressure value of said pressure applying means with said stored pressure value, said control means produces an additional driving signal when the former is not greater than the latter, and said pressure means pressurizes again said pressure applying means in response to said additional driving signal, wherein said control means repeatedly produces said additional driving signal until the pressure of said pressure applying means reaches a predetermined value.

* * * * *